United States Patent
Wang et al.

(10) Patent No.: US 11,399,780 B2
(45) Date of Patent: Aug. 2, 2022

(54) METHODS AND SYSTEMS FOR STATIONARY COMPUTED TOMOGRAPHY

(71) Applicant: RENSSELAER POLYTECHNIC INSTITUTE, Troy, NY (US)

(72) Inventors: Ge Wang, Loudonville, NY (US); Qingsong Yang, Troy, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/347,828

(22) PCT Filed: Nov. 7, 2017

(86) PCT No.: PCT/US2017/060365
§ 371 (c)(1),
(2) Date: May 7, 2019

(87) PCT Pub. No.: WO2018/085824
PCT Pub. Date: May 11, 2018

(65) Prior Publication Data
US 2019/0261930 A1    Aug. 29, 2019

Related U.S. Application Data (60) Provisional application No. 62/580,724, filed on Nov. 2, 2017, provisional application No. 62/421,581, filed
(Continued)

(51) Int. Cl.
*A61B 6/03* (2006.01)
*A61B 5/055* (2006.01)
(Continued)

(52) U.S. Cl.
CPC .............. *A61B 6/032* (2013.01); *A61B 5/055* (2013.01); *A61B 6/03* (2013.01); *A61B 6/4014* (2013.01);
(Continued)

(58) Field of Classification Search
None
See application file for complete search history.

(56) References Cited

U.S. PATENT DOCUMENTS

| 7,085,352 B2 * | 8/2006 | Dunham | A61B 6/032 313/373 |
| 2004/0114710 A1 * | 6/2004 | Ozaki | G06T 11/005 378/9 |

(Continued)

OTHER PUBLICATIONS

International Search Report and The Written Opinion, International Patent Application No. PCT/US2017/060365, dated Jan. 19, 2018.

*Primary Examiner* — Hoon K Song
(74) *Attorney, Agent, or Firm* — Murtha Cullina LLP; Anthony P. Gangemi (57) ABSTRACT

Methods and systems for stationary computed tomography are disclosed. The methods and systems include a gantry having alternating x-ray sources and x-ray detectors that are stationary during operation of the system. The gantry and pairs of x-ray sources and detectors substantially surrounds an object positioned inside the gantry during operation of the system. Dynamically adjustable collimators are positioned between the x-ray sources and the object. Each of the x-ray sources projects an x-ray beam through the collimators and through the object and the x-ray detectors receive the x-ray beam. The x-ray detectors include means for converting the x-ray beam to raw image data. One or more microprocessors control the x-ray sources and the process raw image data. A data storage device stores instructions, which upon execution by the microprocessor, control the x-ray sources and
(Continued)

process the raw image data by converting the raw image data to a digital image.

30 Claims, 8 Drawing Sheets

Related U.S. Application Data on Nov. 14, 2016, provisional application No. 62/418,307, filed on Nov. 7, 2016.

(51) Int. Cl.
*A61B 6/00* (2006.01)
*A61B 6/06* (2006.01)
*G01N 23/046* (2018.01)

(52) U.S. Cl.
CPC ............... *A61B 6/06* (2013.01); *A61B 6/584* (2013.01); *G01N 23/046* (2013.01); *G01N 2223/419* (2013.01)

(56) References Cited

U.S. PATENT DOCUMENTS

| | | | |
|---|---|---|---|
| 2007/0009088 A1 | 1/2007 | Edic et al. | |
| 2007/0025497 A1* | 2/2007 | Fujita | A61B 6/4014 378/9 |
| 2010/0290586 A1* | 11/2010 | Friedrich | A61N 5/1049 378/44 |
| 2012/0288056 A1 | 11/2012 | Murakoshi et al. | |
| 2013/0230135 A1 | 9/2013 | Hoshino et al. | |
| 2015/0016587 A1* | 1/2015 | Baek | G21K 1/02 378/10 |
| 2015/0230766 A1 | 8/2015 | Wang et al. | |
| 2015/0282774 A1* | 10/2015 | Lee | A61B 6/482 378/8 |
| 2015/0305697 A1* | 10/2015 | Tamura | A61B 6/4014 378/5 |
| 2016/0007938 A1* | 1/2016 | Sodickson | A61B 6/482 378/4 |

* cited by examiner

METHODS AND SYSTEMS FOR STATIONARY COMPUTED TOMOGRAPHY

CROSS REFERENCE TO RELATED APPLICATION(S)

This application claims the benefit of U.S. Provisional Application Nos. 62/418,307, filed Nov. 7, 2016; 62/421,581, filed Nov. 14, 2016; and 62/580,724, filed Nov. 2, 2017, each of which is incorporated by reference as if disclosed herein in its entirety.

STATEMENT REGARDING FEDERALLY SPONSORED RESEARCH OR DEVELOPMENT

This invention was made with government support under grant no. R01 EB016977 awarded by the National Institutes of Health. The government has certain rights in the invention.

BACKGROUND

Cardiovascular disease (CVD) is the leading cause of death in the United States for both men and women and a major cause of disability. As reported by the Centers for Disease Control and Prevention, each year 610,000 Americans die from CVD, accounting for 1 in every 4 deaths, and about 735,000 have heart attacks. Given the prevalence of this disease, powerful imaging tools enabling early detection, particularly before symptom presentation, have a major health outcomes impact. The availability of dual source whole body human CT scanners now permits accurate assessment of global cardiac functional parameters as well as quantification of time-dependent variables and reliable evaluation of regional wall motion.

Further, a variety of genetically engineered mouse models have been developed for preclinical studies of factors contributing to coronary disease such as the formation of atherosclerotic plaques in the apoE-deficient mouse. The availability of these mouse models opens the door to in vivo assessment of the processes leading to and following myocardial infarction. However, these mouse models also present new challenges to imaging scientists. First, the murine heart is only about 7 mm along the long axis demanding spatial resolution far greater than that necessary for human heart imaging. Second, the mouse heart beats at up to about 600 bpm (about 10 times faster than the human heart) requiring superior temporal resolution if motion blur is to be minimized. Insufficient data acquisition speed causes image artifacts deforming features and compromising diagnosis. Hence, dedicated imaging systems with very high spatial and temporal resolution are used for non-invasive cardiac assessment in mouse models of human CVD.

Contemporary small animal micro-CT systems using fixed target micro-focus x-ray sources and flat panel digital detectors were first developed in the early 2000s. Available micro-CT systems have adopted the conventional CT architecture in which an x-ray tube and an associated detector array are rotated around an object. Commercial micro-CT scanners are currently available both as stand-alone CT scanners, e.g., GE Healthcare, SCANCO, Perkin-Elmer, and MILabs, and as part of multimodal systems, e.g., Siemens, MILabs, GE Healthcare, and Trifoil Imaging. The vast majority of micro-CT systems use a third generation cone-beam geometry in which the tube and a flat digital detector rotate together around an object in either a step-and-shoot or continuous fashion. However, these systems are not designed for the short exposure time (about 10 ms) necessary for artifact-free murine cardiac CT. Since the temporal resolution of a CT scanner is mainly limited by the rotation speed of the CT gantry, the rotation speed of the gantry remains a bottleneck for temporal resolution improvement. Stationary systems could reduce scan time and system cost, however to date no stationary micro-CT system has been successfully developed.

SUMMARY

Some embodiments of the disclosed subject matter include a method of imaging an object using stationary computed tomography, which include the following steps: positioning an object on a stationary platform; encircling the object with a gantry including x-ray sources positioned at predetermined intervals along the gantry and x-ray detectors positioned at predetermined intervals between each of the x-ray sources along the gantry so that each of the x-ray detectors is positioned to receive an x-ray beam from one of the x-ray sources thereby defining a symmetrical sampling pattern with respect to the object; and activating one or more of the x-ray sources so that x-ray beams are projected from the one or more of the x-ray sources at the object and the x-ray detectors.

Some embodiments of the disclosed subject matter include a stationary computed tomography system having the following interconnected components: a gantry including a body that defines an internal volume and is configured to substantially surround a stationary surface and an object positioned on the stationary surface and within the internal volume during operation of the system; x-ray sources positioned at predetermined intervals along the body of the gantry, each of the x-ray sources configured to project an x-ray beam at the object; x-ray detectors positioned at predetermined intervals between each of the x-ray sources along the body of the gantry so that each of the x-ray detectors is positioned to receive the x-ray beam from one of the x-ray sources, the x-ray detectors including means for converting the x-ray beam to raw image data; one or more collimators movably positioned adjacent to one of the x-ray sources and between one of the x-ray sources and an object so that the x-ray beam passes through the one or more collimators before passing through the object during operation of the system; an x-ray control module including a microprocessor configured to control the x-ray sources and a data storage device configured to store instructions, which upon execution by the microprocessor, control the x-ray control module to perform acts of adjusting settings of the x-ray sources including activating and deactivating the x-ray sources; and an image module including a microprocessor configured to process the raw image data and a data storage device configured to store instructions, which upon execution by the microprocessor, control the image module to perform acts of converting the raw image data to a digital image of the object. The gantry, the x-ray sources, and the x-ray detectors are constructed to be stationary during operation of the system and the x-ray sources and the x-ray detectors are positioned on the gantry so that the raw image data is collected over a symmetric sampling pattern with respect to the object.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
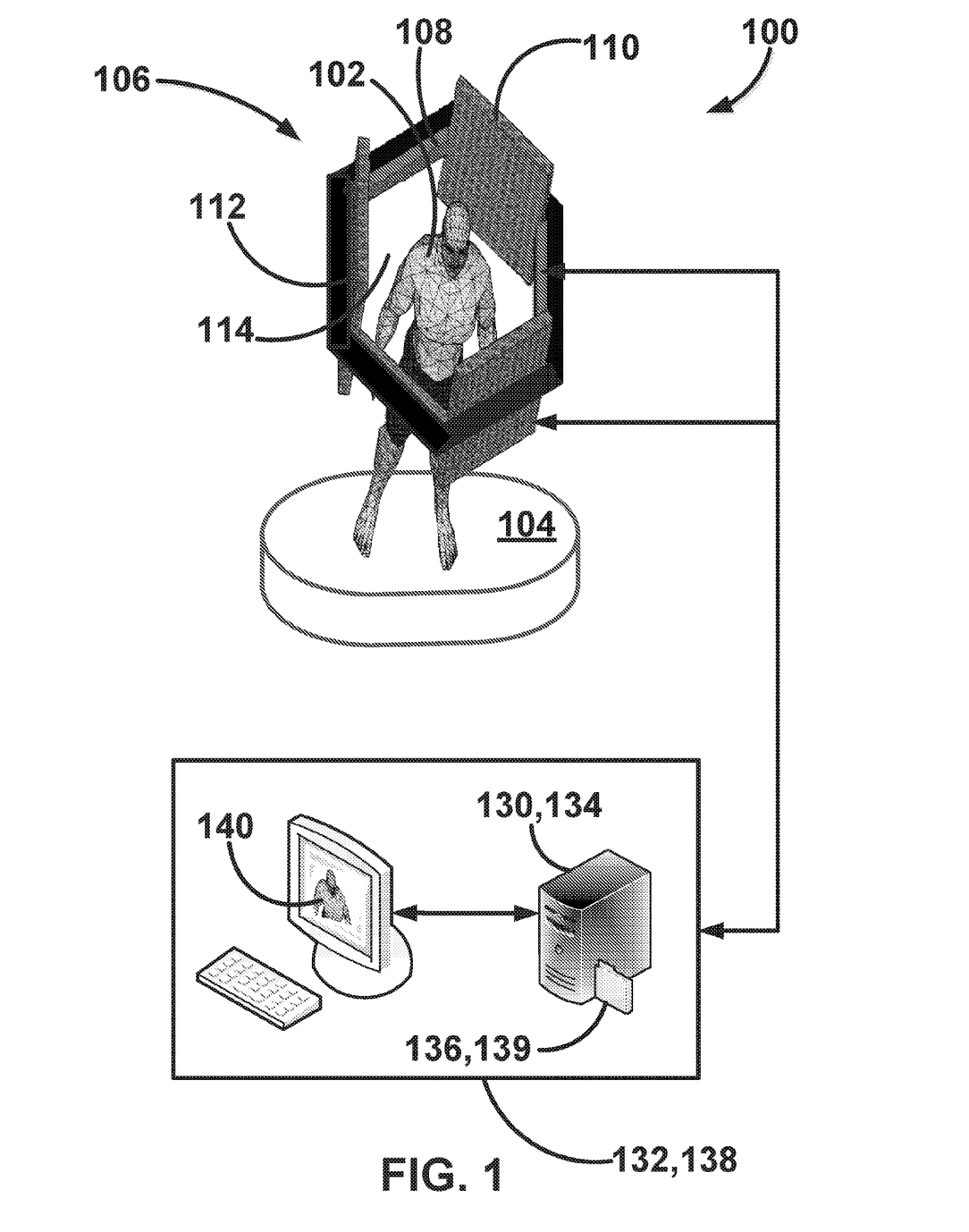
FIG. 1 is a schematic diagram of methods and systems according to some embodiments of the disclosed subject matter.
Figure 2:
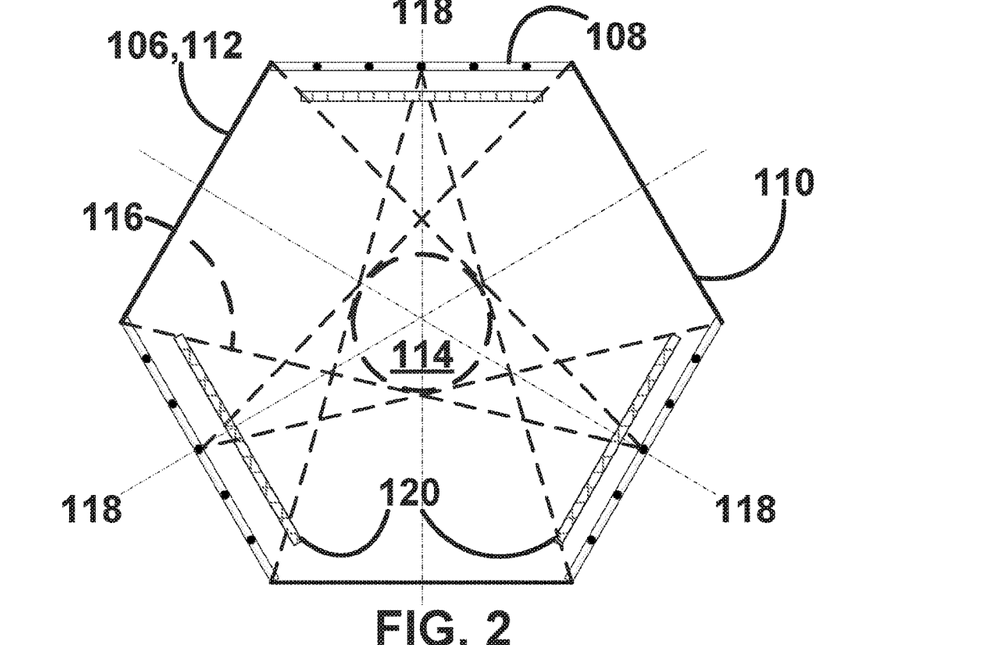
FIG. 2 is a top view of a schematic diagram of a gantry including alternating pairs of x-ray sources and x-ray detectors according to some embodiments of the disclosed subject matter.
Figure 3:
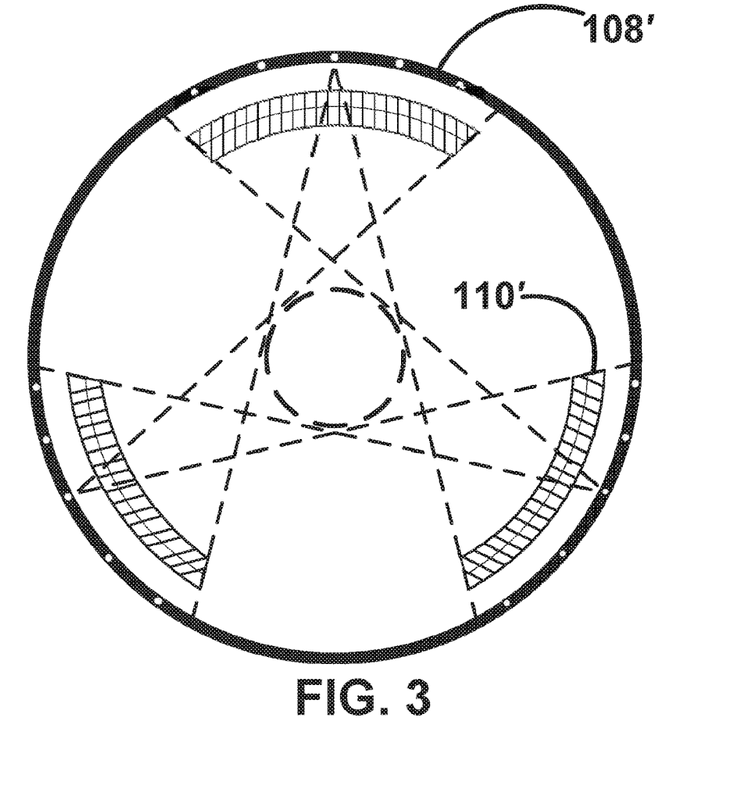
FIG. 3 is a top view of a schematic diagram of a gantry including alternating pairs of x-ray sources and x-ray detectors according to some embodiments of the disclosed subject matter.
Figure 4:
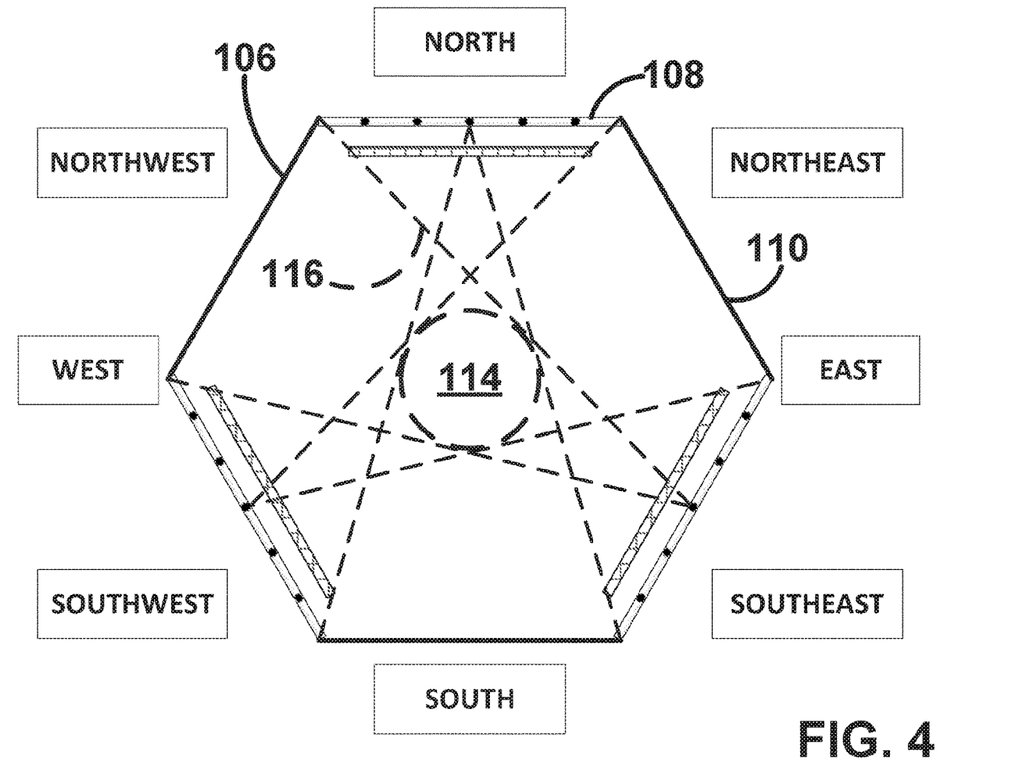
FIG. 4 is a top view of a schematic diagram of a gantry including alternating pairs of x-ray sources and x-ray detectors according to some embodiments of the disclosed subject matter.
Figure 5:
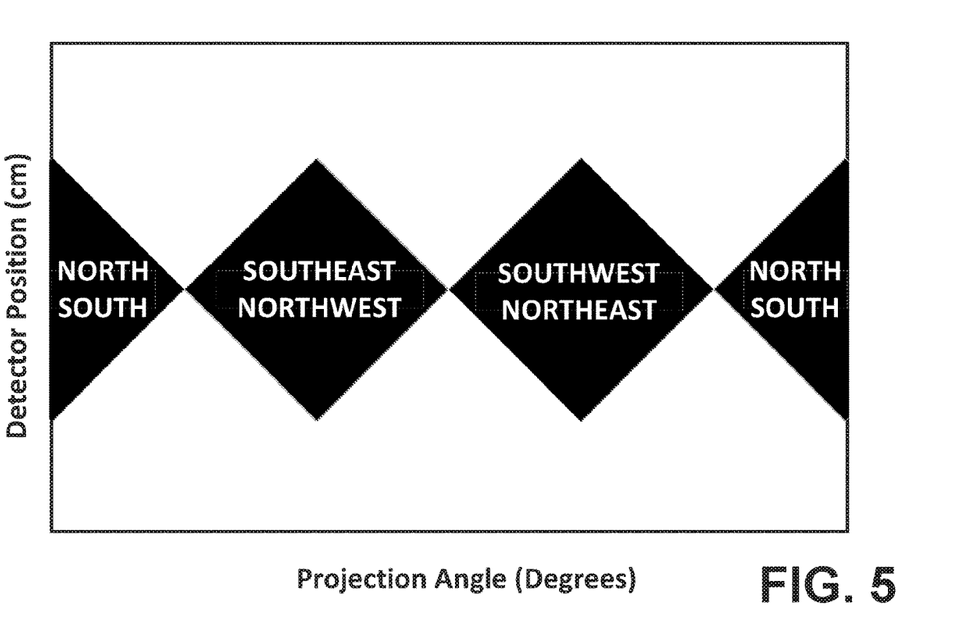
FIG. 5 is a chart showing the symmetric sampling area or pattern of data collected by methods and systems according to some embodiments of the disclosed subject matter.

Referring now to FIGS. 1-3, aspects of the disclosed subject matter include a stationary computed tomography system 100 for both small region of interest (ROI) and whole body imaging of an object 102. In some embodiments, system 100 includes a platform 104 that supports object 102, which is surrounded or encircled by a gantry 106. Gantry 106 includes alternating pairs of x-ray sources 108 and x-ray detectors 110. Platform 104, gantry 106, x-ray sources 108, and x-ray detectors 110 are constructed to be stationary during operation of system 100.

Referring now to FIG. 1, in some embodiments, platform 104 supports object 102, which is to be imaged using system 100. Platform 104 is stationary during operation of system 100. In some embodiments, object 102 is positioned on a stationary surface other than platform 104, e.g., the floor of the room in which system 100 is located.

Gantry 106 includes a body 112 that defines an internal volume 114 and is configured to substantially surround platform 104 and object 102, when it is positioned within the internal volume during operation of system 100. For example, gantry 106 may include a circular, hexagonal, or other shape where an open interior of the shape is internal volume 114.

Referring now to FIG. 2, x-ray sources 108 are positioned at predetermined intervals along body 112 of gantry 106. Each of x-ray sources 108 is configured to project an x-ray beam 116 at object 102. In some embodiments, x-ray sources 108 include cold-cathode multi-spot arrays. However, other types of x-ray sources may be used in system 100 providing they meet performance parameters, e.g., generate images with sufficient resolution, etc., for a particular application. Although shown as linear in FIGS. 1 and 2, as shown in FIG. 3, in some embodiments, x-ray sources 108' have a curvilinear shape.

X-ray detectors 110 are positioned at predetermined intervals between each of x-ray sources 108 along body 112 of gantry 106 so that each of the x-ray detectors is positioned to receive an x-ray beam 116 from one of the x-ray sources. X-ray detectors 110 include standard imaging components (not shown) as means for converting x-ray beams 116 to raw image data (not shown). Although shown as linear flat panel two-dimensional arrays in FIGS. 1 and 2, as shown in FIG. 3, in some embodiments, x-ray detectors 110' have a curvilinear shape.

Referring still to FIG. 2, in some embodiments, system 100 includes three opposing pairs of x-ray sources 108 and x-ray detectors 110 positioned at 120 degrees apart from center line 118 to center line 118 along gantry 106. In other embodiments, system 100 includes any number of opposing pairs of x-ray sources 108 and x-ray detectors 110 positioned at an equal distance from one another along gantry 106 when measured from center line 118 to center line 118, e.g., greater than three opposing pairs. As shown in FIGS. 2 and 3, x-ray sources 108 and x-ray detectors 110 are positioned symmetrically on gantry 106 so that the raw image data of object 102 is collected over a symmetric sampling area or pattern.

Figure 6:
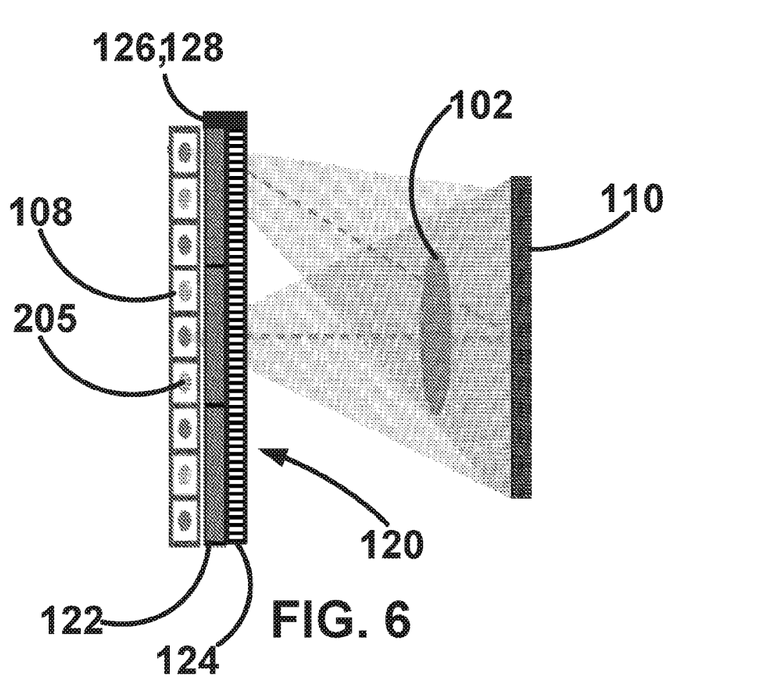
FIG. 6 is a top plan partial view of a schematic diagram of a gantry including an x-ray source and x-ray detector pair and collimator according to some embodiments of the disclosed subject matter.
Figure 7:
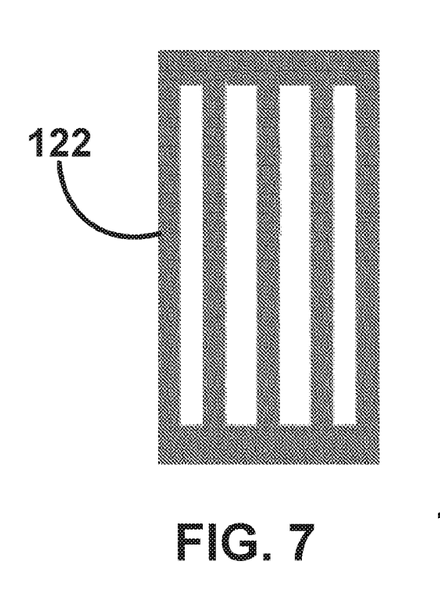
FIG. 7 is a layer of grating of a collimator according to some embodiments of the disclosed subject matter.
Figure 8:
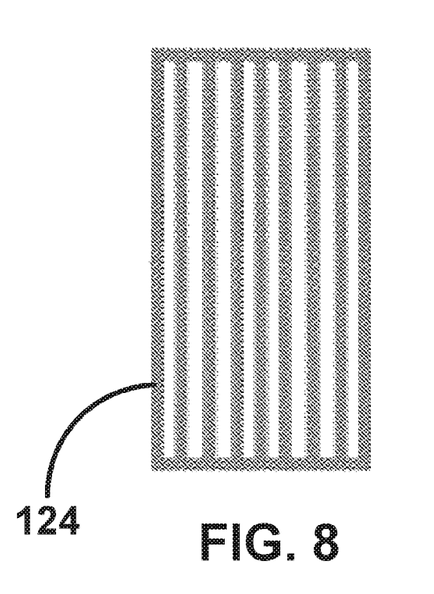
FIG. 8 is a layer of grating of a collimator according to some embodiments of the disclosed subject matter.
Figure 9:
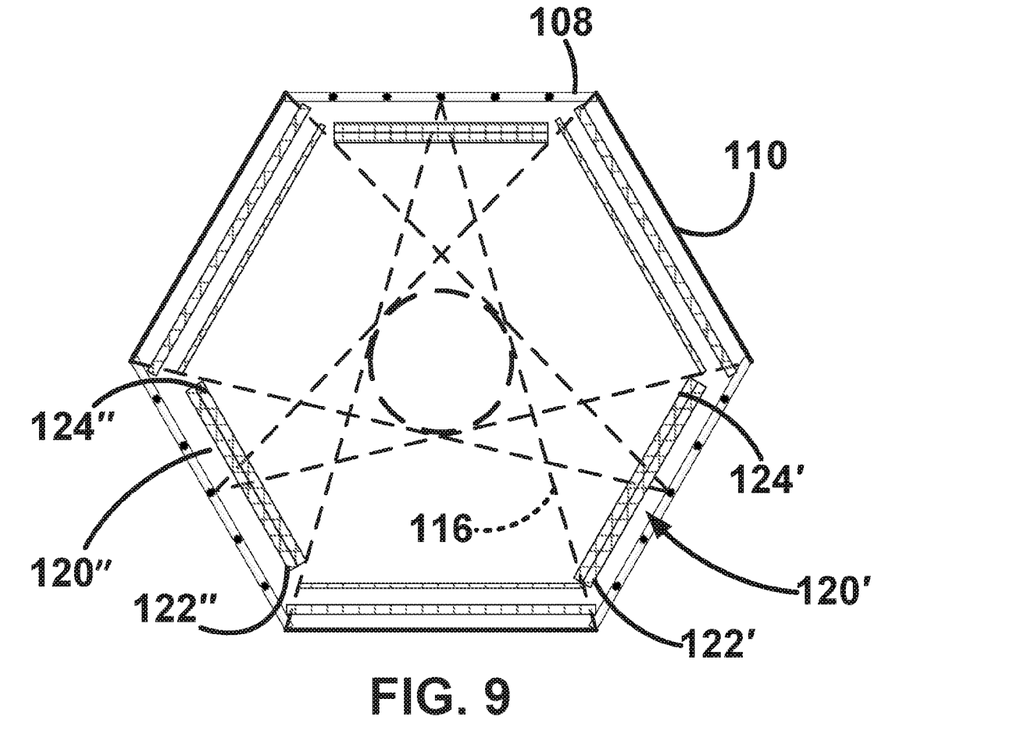
FIG. 9 is a is a top view of a schematic diagram of a gantry including alternating pairs of x-ray sources and x-ray detectors and collimators according to some embodiments of the disclosed subject matter.
Figure 10:
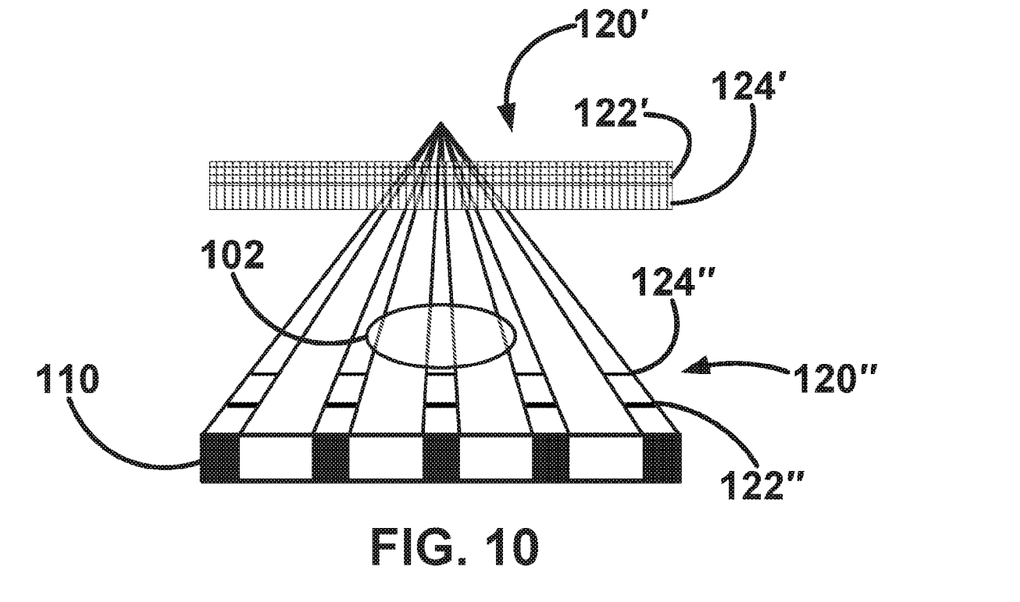
FIG. 10 is an enlarged partial top view of an x-ray beam extending thru a collimator, an object, a second collimator, and into an x-ray detector according to some embodiments of the disclosed subject matter.

Referring now to FIGS. 2-4 and 6-8, in some embodiments, system 100 includes one or more collimators 120 movably and/or adjustably positioned adjacent to one of x-ray sources 108 and between one of the x-ray sources and object 102 so that x-ray beam 116 passes through the one or more collimators before passing through the object during operation of the system. As shown in FIGS. 6-8, in some embodiments, one or more collimators 120 include multiple layers of gratings, e.g., layer 122 and layer 124. Some embodiments include mechanisms 126 joined with one or more of layers 122 and 124 of gratings and a piezoelectric control 128 joined with the mechanisms so that when activated the mechanisms move thereby causing one or more of layers 122 and 124 of gratings to move. This allows adjustment of one or more collimators 120 to more accurately direct x-ray beams 116 toward object 102 and x-ray detectors 110.

Referring now to FIGS. 9-13, in some embodiments, system 100 includes one or more collimators 120' and 120". One or more collimators 120' are movably and/or adjustably positioned adjacent to one of x-ray sources 108 and between one of the x-ray sources and object 102 so that x-ray beam 116 passes through the one or more collimators before passing through the object during operation of system 100.

Figure 11:
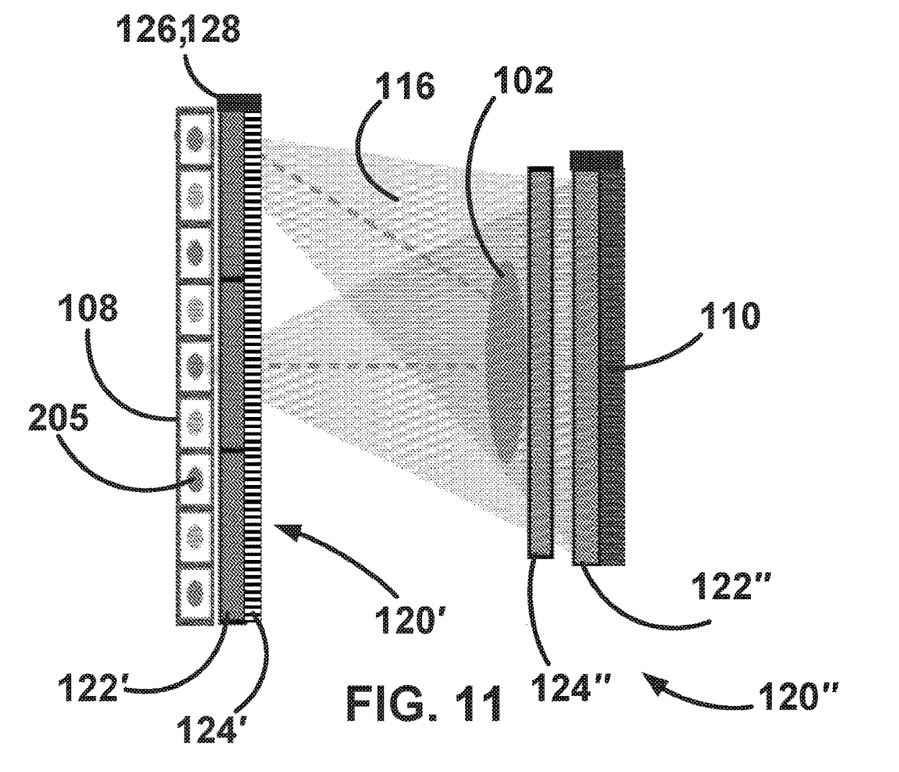
FIG. 11 is a top plan partial view of a schematic diagram of a gantry including an x-ray source and x-ray detector pair and collimators according to some embodiments of the disclosed subject matter.
Figures 12, 13:
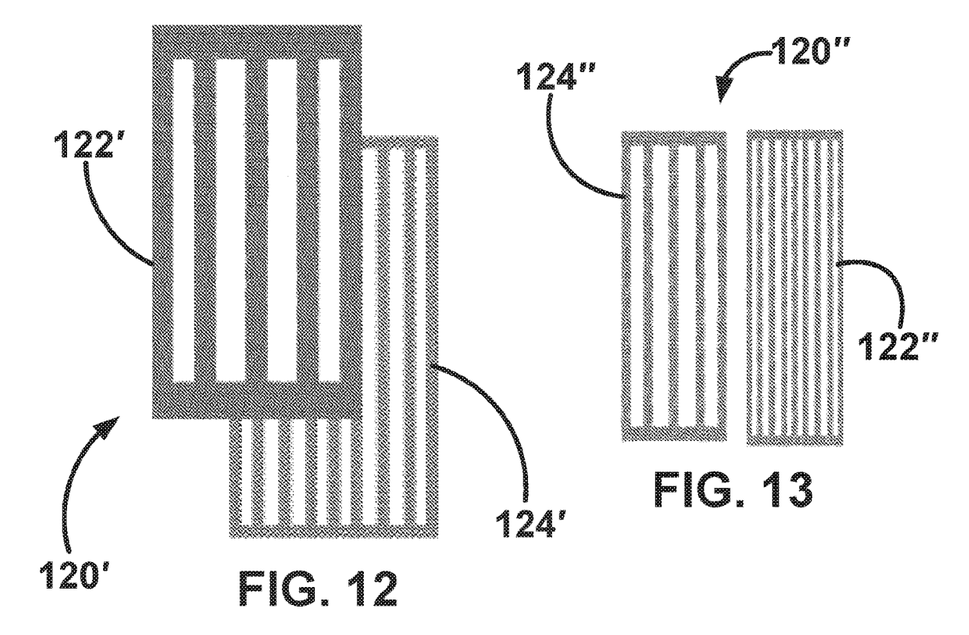
FIG. 12 is two layers of grating of a collimator according to some embodiments of the disclosed subject matter.
FIG. 13 is two layers of grating of a collimator according to some embodiments of the disclosed subject matter.

As shown in FIGS. 11-13, in some embodiments, one or more collimators 120' include multiple layers of gratings, e.g., layer 122' and layer 124'. In some embodiments, one or more collimators 120" are movably and/or adjustably positioned between object 102 and x-ray detectors 110. In some embodiments, one or more collimators 120" include multiple layers of gratings, e.g., layer 122" and layer 124". Some embodiments include mechanisms 126 joined with one or more of layers 122',124', 122", 124" of gratings and a piezoelectric control 128 joined with the mechanisms so that when activated the mechanisms move thereby causing one or more of layers 122',124', 122", 124" of gratings to move. This allows adjustment of one or more collimators 120' and 120" to more accurately direct x-ray beams 116 toward object 102 and x-ray detectors 110.

Referring again to FIG. 1, in some embodiments, system 100 includes one or more microprocessors 130 for controlling x-ray sources 108 and x-ray detectors 110. In some embodiments, system 100 includes an x-ray control module 132 including microprocessor 130, which is configured to control x-ray sources 108, and a data storage device 134, which is configured to store instructions 136. Upon execution by microprocessor 130, instructions 136 control x-ray control module 132 and cause it to perform acts such as adjusting settings of x-ray sources 108 including activating and deactivating the x-ray sources. In some embodiments, microprocessor 130 and instructions 134 of x-ray control module 132 are configured to control piezoelectric control 128 to input and adjust settings for one or more collimators 120, 120', and 120".

Still referring to FIG. 1, in some embodiments, system 100 includes an image module 138 including microprocessor 130 or similar, which is configured to process raw image data (not shown) collected by x-ray detectors 110 and a data storage device 134 or similar, which is configured to store instructions 139. Upon execution by microprocessor 130, instructions 138 control image module 138 and cause it to perform acts such as converting the raw image data to a digital image 140 of object 102.

Figure 14:
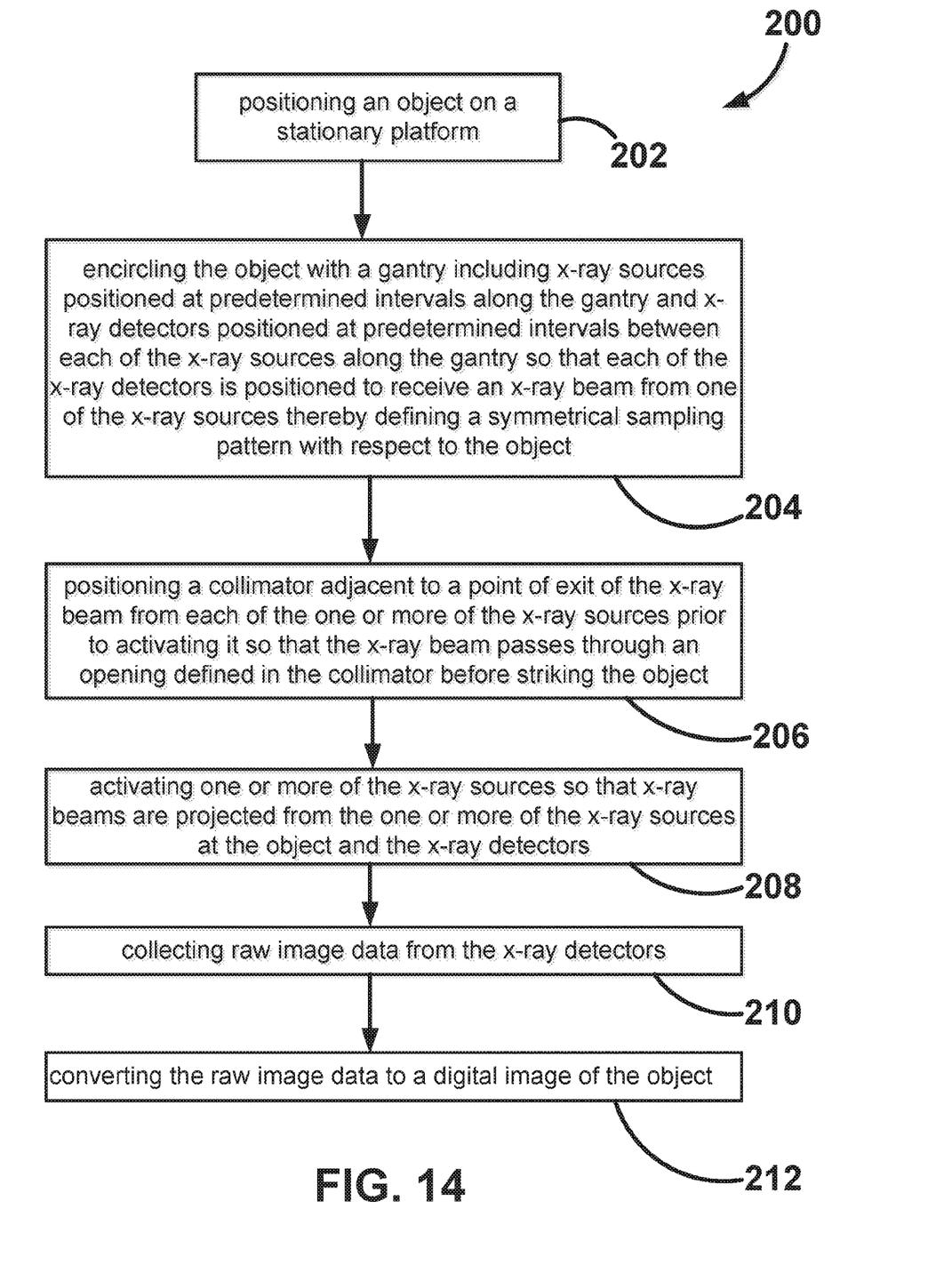
FIG. 14 is a chart of a method according to some embodiments of the disclosed subject matter.
Figure 15A:
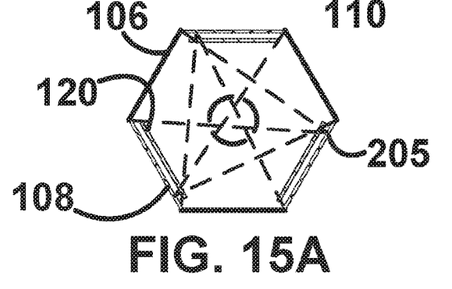
FIGS. 15A-15E is a schematic diagram showing the sequential activation of x-ray source spots in methods and systems according to some embodiments of the disclosed subject matter.
Figure 15B:
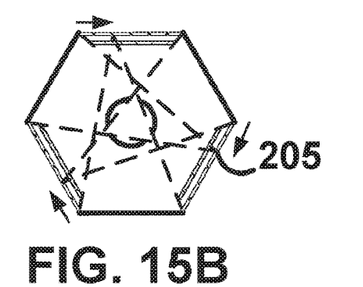
Figure 15C:
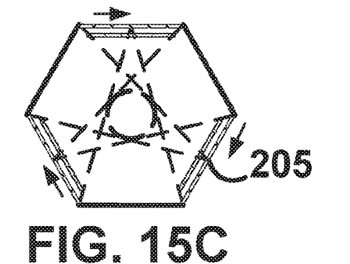
Figure 15D:
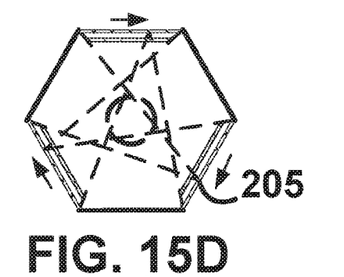
Figure 15E:
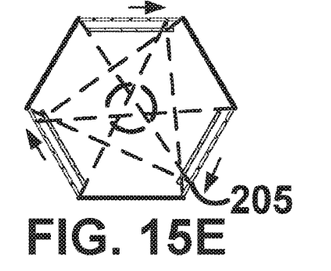

Referring now to FIG. 14, some embodiments include a method 200 of imaging an object using stationary computed tomography. At 202, an object is positioned on a stationary platform. At 204, the object is encircled with a gantry including x-ray sources positioned at predetermined intervals along the gantry and x-ray detectors positioned at predetermined intervals between each of the x-ray sources along the gantry so that each of the x-ray detectors is positioned to receive an x-ray beam from one of the x-ray sources thereby defining a symmetrical sampling pattern with respect to the object. As shown in FIGS. 15A-15E, in some embodiments, each of the one or more of the x-ray sources is activated in a predetermined sequential order or a plurality of source spots 205 on each of the one or more of the x-ray sources is activated in a predetermined sequential order. In some embodiments, multiple x-ray sources or source spots are activated simultaneously. At 206, a collimator is positioned and/or adjusted adjacent to a point of exit of the x-ray beam from each of the one or more of the x-ray sources and/or each of the plurality of source spots on each of the one or more of the x-ray sources prior to activating it so that the x-ray beam passes through an opening defined in the collimator before striking the object. At 208, one or more of the x-ray sources is activated so that x-ray beams are projected from the one or more of the x-ray sources at the object and the x-ray detectors. At 210, raw image data is collected from the x-ray detectors. At 212, the raw image data is converted to a digital image of the object.

Methods and systems according the disclosed subject matter offer advantages over known technology. An interlaced x-ray source and x-ray detector configuration according to the disclosed subject matter provides angularly symmetric image data, which allows images to be reconstructed in a compressed sensing framework. Aspects of the disclosed subject matter including dynamic, anti-scatter collimators having adjustable grating layers reduces the scatter to primary ratio to a level where images generated using systems and methods according to the disclosed subject matter are clinically relevant. Methods and systems according the disclosed subject matter yield good quality reconstructions over a large field of view, e.g., whole body scans, and even higher quality within smaller interior regions of interest.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of imaging an object using stationary computed tomography, said method comprising:
    positioning an object on a stationary platform;
    encircling said object with a gantry including x-ray sources positioned at intervals along said gantry and x-ray detectors positioned at intervals between each of said x-ray sources along said gantry so that each of said x-ray detectors is positioned on a radially opposite side of said gantry from one of said x-ray sources, wherein each of said x-ray detectors is configured to receive an x-ray beam from said one of said x-ray sources; and
    activating one or more of said x-ray sources so that x-ray beams are projected from said one or more of said x-ray sources at said object and said x-ray detectors,
    wherein first collimators are each positioned adjacent to a respective x-ray source of said x-ray sources and between said respective x-ray source and said object so that said x-ray beams pass through said first collimators before passing through said object, and
    wherein each of said first collimators comprises a first grating layer and a second grating layer.

2. The method according to claim 1, further comprising activating each of said one or more of said x-ray sources in a sequential order.

3. The method according to claim 2, further comprising:
    collecting raw image data from said x-ray detectors; and
    converting said raw image data to a digital image of said object.

4. The method according to claim 1, further comprising activating a plurality of source spots on each of said one or more of said x-ray sources in a sequential order.

5. A stationary computed tomography system, comprising:
    a platform for supporting an object to be imaged using said system;
    a gantry that defines an internal volume and is configured to substantially surround said platform and said object positioned within said internal volume during operation of said system;
    x-ray sources positioned at intervals along said gantry, each of said x-ray sources being configured to project an x-ray beam at said object;

x-ray detectors positioned at intervals between each of said x-ray sources along said gantry so that each of said x-ray detectors is positioned on a radially opposite side of said gantry from one of said x-ray sources, wherein each of said x-ray detectors is configured to receive an x-ray beam from said one of said x-ray sources, and wherein said x-ray detectors include means for converting x-ray beams to raw image data; and first collimators each positioned adjacent to a respective x-ray source of said x-ray sources and between said respective x-ray source and said object so that said x-ray beams pass through said first collimators before passing through said object during operation of said system, each of said first collimators comprising a first grating layer and a second grating layer, wherein said platform, said gantry, said x-ray sources, and said x-ray detectors are configured to be stationary during operation of said system, and said x-ray sources and said x-ray detectors are positioned on said gantry so that said raw image data is collected over a symmetric sampling pattern with respect to said object.

6. The system according to claim 5, further comprising:
one or more microprocessors configured to control said x-ray sources and to process said raw image data; and
a data storage device configured to store instructions, which upon execution by said microprocessor, control said x-ray sources to activate and deactivate said x-ray sources, and process said raw image data by converting said raw image data to a digital image of said object.

7. The system according to claim 5, wherein said x-ray sources include cold-cathode multi-spot arrays.

8. The system according to claim 5, wherein said x-ray sources and said x-ray detectors have a curvilinear shape.

9. The system according to claim 5, wherein said x-ray detectors are flat panel two-dimensional arrays.

10. The system according to claim 5, further comprising:
mechanisms joined with either one or both of said first grating layer and said second grating layer; and
a piezoelectric control joined with said mechanisms so that when activated, said mechanisms move thereby causing either one or both of said first grating layer and said second grating layer to move.

11. The system according to claim 5, wherein said x-ray sources and said x-ray detectors comprise more than two opposing pairs of x-ray sources and x-ray detectors positioned at an equal distance from one another along said gantry when measured from center line to center line.

12. The system according to claim 5, wherein said x-ray sources and said x-ray detectors comprise three opposing pairs of x-ray sources and x-ray detectors positioned at 120 degrees apart from center line to center line along said gantry.

13. A stationary computed tomography system, comprising:
a gantry that defines an internal volume and is configured to substantially surround a stationary surface and an object positioned on said stationary surface and within said internal volume during operation of said system;
x-ray sources positioned at intervals along said gantry, each of said x-ray sources being configured to project an x-ray beam at said object;
x-ray detectors positioned at intervals between each of said x-ray sources along said gantry so that each of said x-ray detectors is positioned on a radially opposite side of said gantry from one of said x-ray sources, wherein each of said x-ray detectors is configured to receive an x-ray beam from said one of said x-ray sources, and wherein said x-ray detectors include means for converting x-ray beams to raw image data;
first collimators each positioned adjacent to a respective x-ray source of said x-ray sources and between said respective x-ray source and said object so that said x-ray beams pass through said first collimators before passing through said object during operation of said system, each of said first collimators comprising a first grating layer and a second grating layer;
an x-ray control module including a microprocessor configured to control said x-ray sources; and
a data storage device configured to store first instructions, which upon execution by said microprocessor, control said x-ray control module to activate and deactivate said x-ray sources,
wherein said data storage device is further configured to store second instructions, which upon execution by said microprocessor, control an image module to convert said raw image data to a digital image of said object,
wherein said gantry, said x-ray sources, and said x-ray detectors are configured to be stationary during operation of said system, and
wherein said x-ray sources and said x-ray detectors are positioned on said gantry so that said raw image data is collected over a symmetric sampling pattern with respect to said object.

14. The system according to claim 13, further comprising:
mechanisms joined with portions of said first collimators; and
a piezoelectric control joined with said mechanisms so that when activated, said mechanisms move thereby causing one or more of said portions of said first collimators to move.

15. The system according to claim 14 wherein said microprocessor is further configured to control said piezoelectric control.

16. The system according to claim 13, wherein said x-ray sources include cold-cathode multi-spot arrays.

17. The system according to claim 13, wherein said x-ray sources and said x-ray detectors have a curvilinear shape.

18. The system according to claim 13, wherein said x-ray sources and said x-ray detectors comprise more than two opposing pairs of x-ray sources and x-ray detectors positioned at an equal distance from one another along said gantry when measured from center line to center line.

19. The method according to claim 4, wherein said activating of said plurality of source spots includes activating said plurality of source spots in sequence according to relative positions of said source spots on said x-ray sources.

20. The method according to claim 19, wherein when one of said plurality of source spots on one of said x-ray sources is activated, a corresponding source spot, among said plurality of source spots, on each remaining x-ray source, among said x-ray sources, is activated.

21. The method according to claim 1, wherein each of said x-ray detectors is positioned on a radially opposite side of said gantry from a corresponding one of said x-ray sources, wherein each of said x-ray detectors is configured to receive an x-ray beam from said corresponding one of said x-ray sources.

22. The method according to claim 1, wherein a respective center of mass of each of said x-ray detectors is positioned on a radially opposite side of said gantry from a respective center of mass of said one of said x-ray sources.

23. The method according to claim 1, wherein said gantry is formed as a polygon, said x-ray sources are respectively disposed on first alternating sides of said polygon, and said x-ray detectors are respectively disposed on second alternating sides of said polygon adjacent to said first alternating sides.

24. The method according to claim 23, wherein said polygon is a hexagon.

25. The system according to claim 5, wherein said first grating layer is disposed between said respective x-ray source and said second grating layer.

26. The system according to claim 25, wherein each of said x-ray sources is linear, and each of said first collimators is linear and parallel with said respective x-ray source.

27. The system according to claim 25, further comprising second collimators each positioned adjacent to a respective x-ray detector of said x-ray detectors, wherein each of said second collimators comprises a third grating layer and a fourth grating layer, and wherein said third grating layer is disposed between said respective x-ray detector and said fourth grating layer.

28. The system according to claim 27, wherein each of said x-ray detectors is linear, and each of said second collimators is linear and parallel with said respective x-ray detector.

29. The system according to claim 27, wherein said object is disposed between said second grating layer and said third grating layer.

30. The method of claim 1, wherein all of said x-ray detectors are coplanar with all of said x-ray sources.

* * * * *